US012408879B2

(12) United States Patent
Lee et al.

(10) Patent No.: US 12,408,879 B2
(45) Date of Patent: Sep. 9, 2025

(54) GAMMA RAY PROBE CAPABLE OF BEING INSERTED INTO HUMAN BODY AND GAMMA RAY DETECTION APPARATUS USING SAME

(71) Applicants: Korea University Research and Business Foundation, Seoul (KR); ARALE laboratory Co., Ltd., Seoul (KR)

(72) Inventors: Hak-Jae Lee, Seoul (KR); Jung-Yeol Yeom, Seoul (KR); Ki-Sung Lee, Seoul (KR); Hyun-Koo Kim, Seoul (KR); Min-Hyuk Park, Seoul (KR)

(73) Assignees: Korea University Research and Business Foundation, Seoul (KR); ARALE laboratory Co., Ltd., Seoul (KR)

( * ) Notice: Subject to any disclaimer, the term of this patent is extended or adjusted under 35 U.S.C. 154(b) by 0 days.

(21) Appl. No.: 18/642,032

(22) Filed: Apr. 22, 2024

(65) Prior Publication Data

US 2025/0169773 A1 May 29, 2025

(30) Foreign Application Priority Data

Nov. 24, 2023 (KR) ........................ 10-2023-0165621

(51) Int. Cl.
*A61B 6/03* (2006.01)
*A61B 6/00* (2024.01)
*A61B 6/42* (2024.01)

(52) U.S. Cl.
CPC ............ *A61B 6/037* (2013.01); *A61B 6/4241* (2013.01); *A61B 6/5205* (2013.01)

(58) Field of Classification Search
CPC ...... A61B 6/037; A61B 6/4241; A61B 6/5205
See application file for complete search history.

(56) References Cited

U.S. PATENT DOCUMENTS

2020/0333478 A1* 10/2020 Ullah .................... G01T 1/2002
2022/0026589 A1* 1/2022 Yeom ....................... G01T 7/00

* cited by examiner

*Primary Examiner* — Chao Sheng
(74) *Attorney, Agent, or Firm* — NSIP Law

(57) ABSTRACT

Proposed are a gamma ray probe capable of being inserted into the human body and a gamma ray detection apparatus using the same. The gamma ray probe includes a collimator, a scintillator array disposed on a rear of the collimator and configured to emit light photons in response to radiation passing through the collimator, a light sensor module disposed on a rear of the scintillator array and configured to detect light photons emitted from the scintillator array and convert the light photons into an electrical signal, a light guide part disposed between the scintillator array and the light sensor module and configured to guide light photons from the scintillator array to the light sensor module, and a cylindrical probe casing accommodating the collimator, the scintillator array, the light sensor module, and the light guide part therein.

10 Claims, 5 Drawing Sheets

GAMMA RAY PROBE CAPABLE OF BEING INSERTED INTO HUMAN BODY AND GAMMA RAY DETECTION APPARATUS USING SAME

CROSS REFERENCE TO RELATED APPLICATION

The present application claims priority to Korean Patent Application No. 10-2023-0165621, filed Nov. 24, 2023, the entire contents of which are incorporated herein for all purposes by this reference.

BACKGROUND OF THE INVENTION

Field of the Invention

The present disclosure relates generally to a gamma ray probe capable of being inserted into the human body and a gamma ray detection apparatus using the same. More particularly, the present disclosure relates to a gamma ray probe capable of being inserted into the human body by being manufactured in a size to be inserted into the human body and a gamma ray detection apparatus using the same.

Description of the Related Art

Nuclear medicine imaging technology is a technology that reconstructs images by injecting and diffusing a small amount of radioactive materials into the human body and detecting gamma rays emitted by radioactive isotopes (tracers) within specific organs, bones, and tissues.

Such a gamma ray imaging technology includes positron emission tomography (PET) and single photon emission computed tomography (SPECT) which are tomographic imaging system of the gamma camera. Unlike CT and MRI, which provide structural images of the living body, PET and SPECT provide biochemical functional images such as a blood flow and cell metabolism, allowing early diagnosis of cancer or disease.

A gamma ray imaging device using gamma ray imaging technology is provided with a gamma camera (or a gamma probe) for detecting photons of gamma rays. Typically, the gamma camera includes a collimator, a scintillation crystal, and a light sensor module.

The collimator is made of a dense material such as lead or tungsten material with holes formed therein, and is used to control the direction of radiation emitted from radioactive isotopes injected into the human body. The collimator allows radiation incident through the hole formed in the collimator to pass, and causes radiation incident at a predetermined angle or more to be shielded.

The scintillation crystal interacts with radiation that has passed through the collimator and emits photons in response to the hitting radiation. The detection position of the photons emitted in this way is determined by the light sensor module, making imaging possible.

Meanwhile, recently, there have been attempts to manufacture the gamma camera in a size to be inserted into the human body in order to apply the gamma camera to minimally invasive robotic arm surgery, and in particular, technology development for imaging is in progress.

However, there are several problems in producing a gamma camera, which can produce images, in a size to be inserted into the human body. For example, for more precise imaging, radiation irradiated in directions other than those through the collimator holes is required to be shielded, but it is not easy to design a gamma camera in which all components are miniaturized and a shield structure is provided.

In gamma ray imaging system, photons converted by the scintillation crystal are transmitted to pixels of the optical sensor through a light guide. Herein, because commonly used light guide does not provide radiation shielding, additional radiation shielding structure or materials are required.

However, it is difficult to insert additional radiation shielding structure or materials in the gamma camera, which can produce images, in the size to be inserted into the human body due to space constraints.

SUMMARY OF THE INVENTION

Accordingly, the present disclosure has been made to solve the above problems occurring in the related art, and the present disclosure is intended to propose a gamma ray probe capable of being inserted into the human body that can be manufactured in a size to be inserted into the human body and can eliminate the effects of unintended radiation and a gamma ray detection apparatus using the same.

In order to achieve the objectives, according to an embodiment of the present disclosure, there is provided a gamma ray probe capable of being inserted into the human body, the gamma ray probe including: a collimator; a scintillator array disposed on a rear of the collimator and configured to emit light photons in response to radiation passing through the collimator; a light sensor module disposed on a rear of the scintillator array and configured to detect light photons emitted from the scintillator array and convert the light photons into an electrical signal; a light guide part disposed between the scintillator array and the light sensor module and configured to guide light photons from the scintillator array to the light sensor module; and a cylindrical probe casing accommodating the collimator, the scintillator array, the light sensor module, and the light guide part therein, wherein the light guide part is made of a material that reacts to radiation and emits light photons, with the material having a characteristic different from a radiation response characteristic of the scintillator array.

Here, the collimator may include a pinhole collimator, and the scintillator array may be inserted into the rear of the pinhole collimator so that a side surface of the scintillator array is shielded by the pinhole collimator.

In addition, the light guide part may emit light photons in response to radiation introduced from a side or rear surface of the probe casing.

Here, the scintillator array may be made of at least one or a combination of two or more of gadolinium aluminium gallium garnet (GAGG), CsI, NaI, and lutetium yttrium orthosilicate (LYSO), and the light guide part may be made of at least one or a combination of two or more of bismuth germanium oxide ($Bi_4Ge_3O_{12}$, BGO), lead tungstate ($PbWO_4$, PWO), cadmium tungstate ($CdWO_4$, CWO), and $Lu_2O_3$.

In addition, a radiation shielding structure may not be formed on a side surface of each of the light sensor module and the light guide part.

Meanwhile, in order to achieve the above objectives, according to another embodiment of the present disclosure, there is provided a gamma ray detection apparatus including the gamma ray probe, and a signal processing device configured to process an electrical signal from the gamma ray probe, wherein the signal processing device separates an electrical signal into which light photons from the light guide part of the gamma ray probe is converted from electrical signals from the light sensor module of the gamma ray probe, and detects a gamma ray on a basis of an electrical signal into which light photons from the scintillator array of the gamma ray probe is converted.

Here, the signal processing device may process and image an electrical signal from the gamma ray probe.

In addition, the signal processing device may separate an electrical signal into which light photons from the light guide part is converted and an electrical signal into which light photons from the scintillator array is converted from each other on a basis of a pulse shape discrimination technique.

Additionally, the pulse shape discrimination technique may include any one of a zero crossing technique, a charge comparison technique, a rise time discrimination technique, a pulse gradient analysis technique, a fuzzy logic technique, a discrete wavelet transform technique, a wavelength discrimination technique, a PSD technique using an autoencoder, and a maximum likelihood (ML)-based PSD technique.

In addition, the signal processing device may separate an electrical signal into which light photons from the light guide part is converted and an electrical signal into which light photons from the scintillator array is converted from each other on a basis of amplitude of an electrical signal from the gamma ray probe.

According to the present disclosure, due to the above configuration, radiation introduced from the side and rear surfaces of the light sensor module and the light guide part on which a radiation shielding design is not easy due to the implementation of the miniaturization of the gamma ray probe to be inserted into the human body is removed through the material of the light guide part and signal processing, thereby enabling more accurate detection and imaging of radiation.

BRIEF DESCRIPTION OF THE DRAWINGS

The above and other objectives, features, and other advantages of the present disclosure will be more clearly understood from the following detailed description when taken in conjunction with the accompanying drawings, in which.

(a) and (b) of FIG. 3 are views illustrating the influx of radiation depending on a material of a light guide part of a gamma ray probe according to the embodiment of the present disclosure.

(a) and (b) of FIG. 4 are views illustrating examples of decay time difference between electrical signals according to scintillators.

DETAILED DESCRIPTION OF THE INVENTION

The advantages and features of the present disclosure, and how to achieve them will be clear by referring to embodiments described in detail below along with the accompanying drawings. However, the present disclosure is not limited to the embodiments disclosed below, but may be implemented in various forms. These embodiments are provided solely to ensure that the disclosure of the present disclosure is complete and to fully inform those skilled in the art to which the present disclosure belongs of the scope of the present disclosure. The present disclosure is only defined by the scope of the claims.

Terms used herein are intended to describe embodiments and are not intended to limit the present disclosure. In this specification, singular forms also include plural forms, unless specifically stated otherwise in the context. As used in the specification, "comprises" and/or "comprising" does not exclude the presence or addition of one or more other elements in addition to mentioned elements. Like reference numerals refer to like elements throughout the specification, and "and/or" includes each and every combination of one or more of the referenced elements. Although "first", "second", etc. are used to describe various components, these components are of course not limited by these terms. These terms are merely used to distinguish one component from another. Accordingly, a first component mentioned below may also be a second component within the technical idea of the present disclosure.

Unless otherwise defined, all terms (including technical and scientific terms) used in this specification may be used to have meanings commonly understood by those skilled in the art to which the present disclosure pertains. Additionally, terms defined in commonly used dictionaries are not interpreted ideally or excessively unless clearly and specifically defined.

Hereinafter, embodiments according to the present disclosure will be described in detail with reference to the attached drawings.

Figure 1:
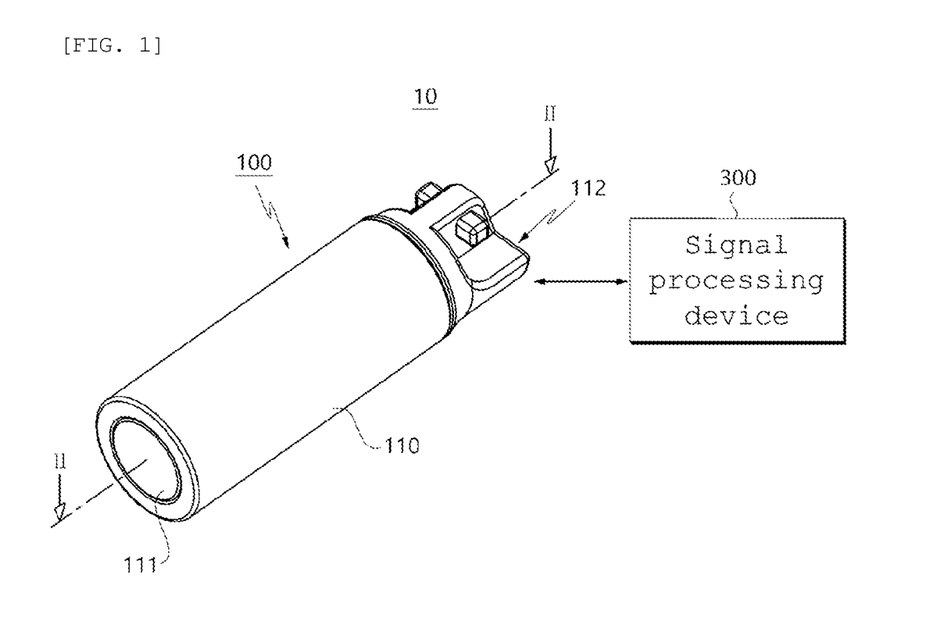
FIG. 1 is a view illustrating the configuration of a gamma ray detection apparatus according to an embodiment of the present disclosure.
Figure 2:
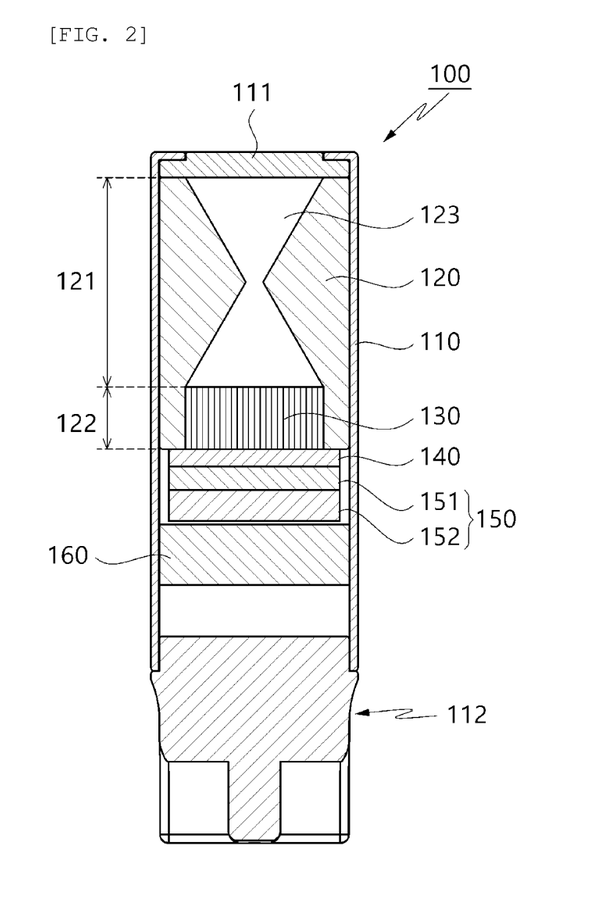
FIG. 2 is a cross-sectional view taken along line II-II of FIG. 1.

FIG. 1 is a view illustrating the configuration of a gamma ray detection apparatus 10 according to an embodiment of the present disclosure, and FIG. 2 is a cross-sectional view taken along line II-II of FIG. 1.

Referring to FIGS. 1 and 2, the gamma ray detection apparatus 10 according to the embodiment of the present disclosure may include a gamma ray probe 100, and a signal processing device.

The gamma ray probe 100 according to the embodiment of the present disclosure is illustrated to be configured to have size and shape to be inserted into the human body. In one embodiment, during robotic cancer surgery, the gamma ray probe of the gamma ray detection apparatus 10 according to the present disclosure, together with a robotic surgical device, is inserted into the human body to detect gamma rays, for example, to perform imaging of lesions.

The gamma ray probe according to the embodiment of the present disclosure may include a collimator 120, a scintillator array 130, a light sensor module 150, a light guide part 140, and a probe casing 110.

The collimator 120 according to the embodiment of the present disclosure guides radiation so that only radiation incident in a predetermined direction among emitted gamma rays reaches the scintillator array 130. The collimator 120 solves the problem of reduced sensitivity due to a small amount of radiation compared to an optical or fluorescence imaging device.

In one embodiment, the collimator 120 is made of a material that shields radiation, for example, tungsten. In addition, in the embodiment of the present disclosure, as the collimator 120, a pinhole collimator 120 is applied.

In one embodiment, as illustrated in FIG. 2, the pinhole collimator 120 according to the embodiment of the present disclosure may be divided into a collimating area 121 with a pinhole area 123 formed therein, and a rear shielding area 122 formed on the rear of the collimating area 121. Here, the scintillator array 130 may be inserted into the rear shielding area 122.

The scintillator array 130 according to the embodiment of the present disclosure is disposed on the rear of the collimator 120. In addition, the scintillator array 130 emits light photons in response to radiation that has passed through the collimator 120. In one embodiment, the scintillator array 130 converts a gamma ray into a low-energy light photons and detects the position of the light photons and a position at which the scintillator array responds to the gamma ray.

In one embodiment, the scintillator array 130 is made of at least one or a combination of two or more of gadolinium aluminium gallium garnet (GAGG), CsI, NaI, and lutetium yttrium orthosilicate (LYSO).

The light sensor module 150 according to the embodiment of the present disclosure may be disposed on a rear of the scintillator array 130. In addition, the light sensor module 150 may detect light photons emitted from the scintillator array 130 and convert the light photons into electrical signals.

In one embodiment, the light sensor module 150 may include a photomultiplier 151 and a circuit board 152. The photomultiplier 151 amplifies light photons from the scintillator array 130, and the circuit board 152 detects the amplitude and position of the light photons amplified by the photomultiplier 151.

In one embodiment, the photomultiplier 151 is implemented as a silicon photomultiplier (SiPM) 151.

The light guide part 140 according to the embodiment of the present disclosure is disposed between the scintillator array 130 and the light sensor module 150. In addition, the light guide part 140 may guide light photons emitted from a position at which interaction of the scintillator array 130 with gamma rays occurs in the scintillator array 130 to the light sensor module 150.

The probe casing 110 according to the embodiment of the present disclosure accommodates and supports the collimator 120, the scintillator array 130, the light sensor module 150, and the light guide part 140. In one embodiment, the probe casing 110 has a cylindrical shape so that the probe casing can be inserted into the human body.

The probe casing 110 has a front cap 111 installed on a front thereof, and thus the front cap 111 shields external foreign substances from being introduced into the probe casing 110. In addition, the probe casing 110 has a rear cap 112 installed on a rear thereof, and a cable to be described later may be connected to the light sensor module 150 through the rear cap 112.

The scintillator array 130 according to the embodiment of the present disclosure is inserted into the rear part of the pinhole collimator 120, that is, into the rear shielding area 122, and thus a side surface of the scintillator array may be shielded by the pinhole collimator 120. As described previously, the pinhole collimator 120 is made of a material that shields radiation, and the side surface of the scintillator array 130 inserted into the rear of the pinhole collimator 120 may be shielded by the pinhole collimator 120. Accordingly, the scintillator array 130 is not affected by radiation introduced in a lateral direction.

Meanwhile, in the embodiment of the present disclosure, the light guide part 140 is made of a material that emits light photons in response to radiation. In addition, as an example, the light guide part 140 emits light photons in response to radiation, but is made of a material with a characteristic different from the radiation response characteristic of the scintillator array 130.

As described previously, the scintillator array 130 is inserted into the rear of the collimator 120, and radiation introduced in a lateral direction is shielded by the collimator 120. However, each of the side surfaces of the light sensor module 150 and the light guide part 140 sometimes cannot have a thick shielding structure due to a miniaturized design for insertion into the human body.

Figure 3:
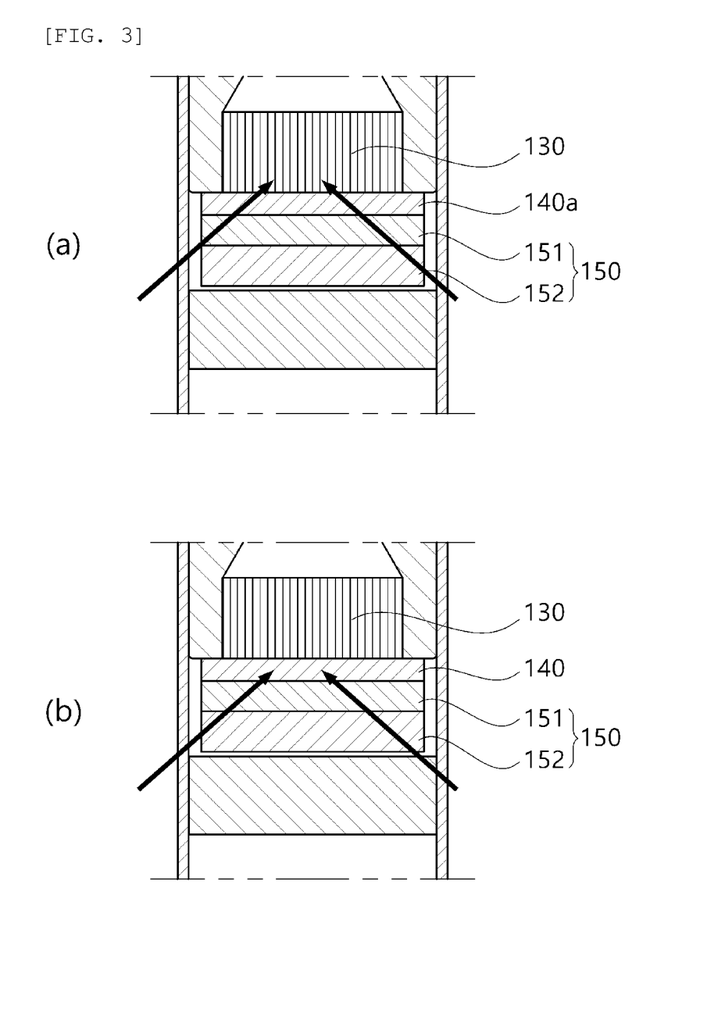

In this case, as illustrated in (a) of FIG. 3, when the light guide part 140 is made of a material that can only guide light, radiation introduced from the side or rear surface of the probe casing 110 may pass through the light sensor module 150 or the light guide part 140 to reach the scintillator array 130.

Accordingly, in a design illustrated in (a) of FIG. 3, the scintillator array 130 reacts to radiation introduced through the light sensor module 150 and the light guide part 140 from the lateral or rear surfaces thereof in addition to radiation passing through the collimator 120, that is, gamma rays, and the radiation introduced from the lateral or rear surfaces eventually acts as noise, thereby deteriorating the quality of an image.

Accordingly, in the present disclosure, as illustrated in (b) of FIG. 3, the light guide part 140, which is made of a material which emits light photons in response to radiation, is made of a material with a characteristic different from the radiation response characteristic of the scintillator array 130. The light guide part 140 is configured to emit light photons in response to radiation introduced from the side surface or rear surface of the probe casing 110 to separate the light photons.

That is, radiation introduced from the side surface or rear surface of the probe casing 110 reacts in the light guide part 140, and is shielded from progressing to the scintillator array 130.

In one embodiment, the scintillator array 130 may be made of gadolinium aluminium gallium garnet (GAGG) as described previously, and the light guide part 140 may be made of at least one or a combination of two or more of bismuth germanium oxide ($Bi_4Ge_3O_{12}$, BGO), lead tungstate ($PbWO_4$, PWO), cadmium tungstate ($CdWO_4$, CWO), and $Lu_2O_3$.

Hereinafter, a method in which the signal processing device according to the above configuration removes the influence of light photons generated in response to radiation introduced from the side or rear surface of the probe casing 110 will be described.

The signal processing device according to the embodiment of the present disclosure may process electrical signals from the gamma ray probe 100, that is, electrical signals caused by light photons detected by the light sensor module 150. In one embodiment, the signal processing device may perform imaging processing to generate a gamma ray image by using an electrical signal from the gamma ray probe 100.

In one embodiment, the signal processing device is connected to the gamma ray probe 100 through the cable and can receive electrical signals from the gamma ray probe 100. Referring to FIG. 1, the probe casing 110 of the gamma ray probe 100 may include the rear cap on a rear thereof, and the connection of the cable may be performed through the rear cap.

Here, the signal processing device separates an electrical signal into which light photons from the light guide part 140 is converted and an electrical signal into which light photons from the scintillator array 130 is converted among electrical signals from the light sensor module 150, and performs gamma ray detection, that is, imaging processing on the basis of the electrical signal into which the light photons from the scintillator array 130 is converted.

As described previously, both the scintillator array 130 and the light guide part 140 emit light photons by reacting to radiation, and are made of materials with different radiation response characteristics, and thus electrical signals can be separated by the signal processing device.

In one embodiment, the signal processing device can separate an electrical signal into which light photons from the light guide part 140 is converted and an electrical signal into which light photons from the scintillator array 130 is converted from each other on the basis of a pulse shape discrimination technique.

The pulse shape discrimination technique is a technique commonly used to distinguish different types of radiation, such as gamma rays, α particles, β particles, and neutrons. More specifically, the pulse shape discrimination technique is a technique in which incident radiation reacts with a detector to produce different shapes of signals depending on the energy, mass, and charge of incident particles, and differences in these signals are used to distinguish the type of radiation.

Such a pulse shape discrimination technique can distinguish not only different types of radiation, but also differences between the same radiation signals that have passed through scintillators with different characteristics. Accordingly, according to the present disclosure, radiation incident on the scintillator array 130 and the light guide part, which have different scintillator materials, is distinguished by using the pulse shape discrimination technique.

In one embodiment, electrical signals detected from scintillators of different materials show difference in decay time. (a) and (b) of FIG. 4 are views illustrating examples of decay time difference between electrical signals according to scintillators.

Figure 4:
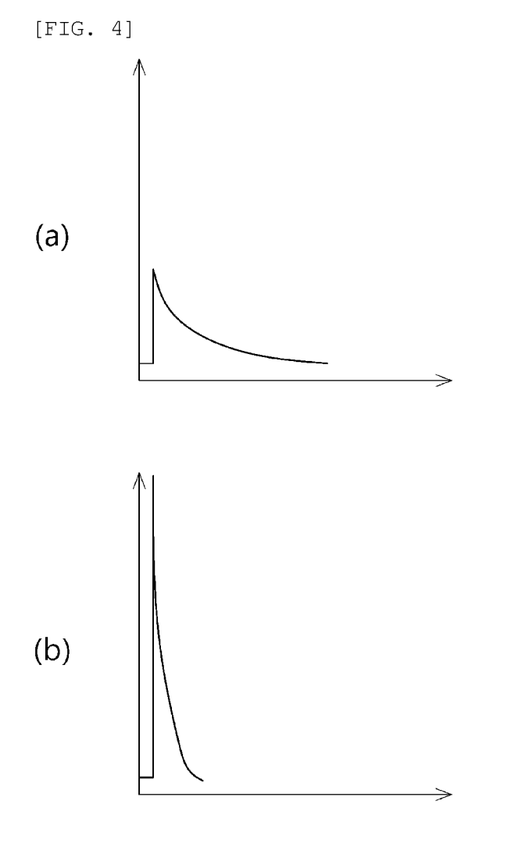

An electrical signal according to a scintillator illustrated in (a) of FIG. 4 is very long in decay time, and is relatively low in amplitude. On the other hand, an electrical signal according to a scintillator illustrated in (b) of FIG. 4 has shorter decay time and higher amplitude
than the electrical signal according to the scintillator illustrated in (a) of FIG. 4.

[Table 1] shows the optical properties of examples of scintillator materials described above.

TABLE 1

| Material | Density(g/cc) | Decay time(ns) | Light quantity (photons/MeV) |
|---|---|---|---|
| GAGG | 6.63~7.08 | 70~100 | 15,000~25,000 |
| BGO | 7.13 | 300 | 8,000~9,000 |
| PWO | 8.28 | 6~12 | 200~300 |
| CWO | 7.9 | 30~60 | 10,000~20,000 |
| Lu$_2$O$_3$ | 9.4 | 1,300,000 | 30,000 |

As described above, when the scintillator array 130 is made of GAGG, and the light guide part 140 is made of BGO, BGO is longer in decay time than GAGG, and thus an electrical signal which is lower in amplitude than an electrical signal according to light photons from the scintillator array 130 and has a long tail is regarded as an electrical signal into which light photons from the light guide part 140 is converted so that the electrical signal can be removed.

In one embodiment, as the pulse shape discrimination technique, any one of a zero crossing technique, a charge comparison technique, a rise time discrimination technique, a pulse gradient analysis technique, a fuzzy logic technique, a discrete wavelet transform technique, a wavelength discrimination technique, a PSD technique using an autoencoder, and a maximum likelihood (ML)-based PSD technique may be applied.

Meanwhile, the signal processing device may separate an electrical signal into which light photons from the light guide part 140 is converted and an electrical signal into which light photons from the scintillator array 130 is converted from each other on the basis of amplitude of an electrical signal from the gamma ray probe 100.

As shown in [Table 1], depending on materials of a scintillator, the amounts of visible light emitted in response to radiation are different from each other. Due to this difference in light quantity, when difference between the amplitudes of electrical signals measured by the light sensor module 150 is significantly large, the signals can be separated by using an appropriate threshold.

Figure 5:
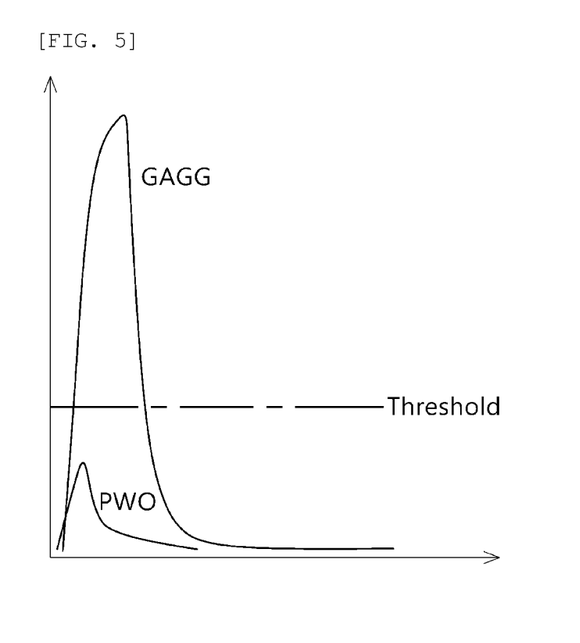
FIG. 5 is a view illustrating an example of difference in amplitude of electrical signals according to scintillators and a threshold.

As an example, among scintillator materials shown in [Table 1], PWO has light quantity of 200 to 300 photons/MeV, and the light quantity of a scintillator made of PWO is only about 1.4% of 15,000 to 20,000 photons/MeV of a scintillator made of GAGG. Accordingly, as shown in FIG. 5, like processing a noise in an electrical signal, by setting a low threshold, it is possible to eliminate an electrical signal into which light photons reacting in the light guide part 140 is converted.

As described above, radiation introduced from the side and rear surfaces of the light sensor module 150 and the light guide part 140 on which a radiation shielding design is not easy due to the implementation of the miniaturization of the gamma ray probe to be inserted into the human body is removed through the material of the light guide part 140 and signal processing, thereby enabling more accurate detection and imaging of radiation.

In the above-described embodiment, it is exemplified that the light guide part 140 reacts to radiation flowing into the side and rear surfaces thereof. On the other hand, as illustrated in FIG. 2, a rear shielding member 160 is installed at the rear of the light guide part 140, specifically, at the rear side of the light sensor module 150 so that radiation introduced from the rear side can be shielded.

Although several embodiments of the present disclosure have been shown and described, those skilled in the art to which the present disclosure belongs will be able to recognize that modifications may be made to the embodiments without departing from the principles or spirit of the present disclosure. The scope of the present disclosure will be determined by the appended claims and equivalents thereto.

What is claimed is:

1. A gamma ray probe capable of being inserted into the human body, the gamma ray probe comprising:
   a collimator;
   a scintillator array disposed on a rear of the collimator and configured to emit light photons in response to radiation passing through the collimator;
   a light sensor module disposed on a rear of the scintillator array and configured to detect light photons emitted from the scintillator array and convert the light photons into an electrical signal;
   a light guide part disposed between the scintillator array and the light sensor module and configured to guide light photons from the scintillator array to the light sensor module; and
   a cylindrical probe casing accommodating the collimator, the scintillator array, the light sensor module, and the light guide part therein, wherein the light guide part is made of a material that reacts to radiation and emits light photons, with the material having a characteristic different from a radiation response characteristic of the scintillator array.

2. The gamma ray probe of claim 1, wherein the scintillator array is made of at least one or a combination of two or more of gadolinium aluminium gallium garnet (GAGG), CSI, NaI, and lutetium yttrium orthosilicate (LYSO), and the light guide part is made of at least one or a combination of two or more of bismuth germanium oxide ($Bi_4Ge_3O_{12}$, BGO), lead tungstate ($PbWO_4$, PWO), cadmium tungstate ($CdWO_4$, CWO), and $Lu_2O_3$.

3. The gamma ray probe of claim 1, wherein a radiation shielding structure is not formed on a side surface of each of the light sensor module and the light guide part.

4. The gamma ray probe of claim 1, wherein the collimator comprises a pinhole collimator, and the scintillator array is inserted into the rear of the pinhole collimator so that a side surface of the scintillator array is shielded by the pinhole collimator.

5. The gamma ray probe of claim 4, wherein the light guide part is configured to emit light photons in response to radiation introduced from a side or rear surface of the probe casing.

6. A gamma ray detection apparatus comprising the gamma ray probe of claim 1, and a signal processing device configured to process an electrical signal from the gamma ray probe, wherein the signal processing device is configured to separate the electrical signal into which light photons from the light guide part of the gamma ray probe is converted from electrical signals from the light sensor module of the gamma ray probe, and to detect a gamma ray on a basis of the electrical signal into which light photons from the scintillator array of the gamma ray probe is converted.

7. The gamma ray detection apparatus of claim 6, wherein the signal processing device is configured to process and image the electrical signal from the gamma ray probe.

8. The gamma ray detection apparatus of claim 6, wherein the signal processing device is configured to separate the electrical signal into which light photons from the light guide part is converted and the electrical signal into which light photons s from the scintillator array is converted from each other on a basis of amplitude of the electrical signal from the gamma ray probe.

9. The gamma ray detection apparatus of claim 6, wherein the signal processing device is configured to separate the electrical signal into which light photons from the light guide part is converted and the electrical signal into which light photons from the scintillator array is converted from each other on a basis of a pulse shape discrimination technique.

10. The gamma ray detection apparatus of claim 9, wherein the pulse shape discrimination technique comprises any one of a zero crossing technique, a charge comparison technique, a rise time technique, a pulse gradient analysis discrimination technique, a fuzzy logic technique, a discrete wavelet transform technique, a wavelength discrimination technique, a PSD technique using an autoencoder, and a maximum likelihood (ML)-based PSD technique.

* * * * *